United States Patent
Bethers et al.

(10) Patent No.: US 10,308,626 B1
(45) Date of Patent: Jun. 4, 2019

(54) CRYSTAL PURIFICATION IN A GLASS OR METAL CONTAINER

(71) Applicants: Pratt Bethers, Arvada, CO (US); David Goodman, III, Federal Heights, CO (US)

(72) Inventors: Pratt Bethers, Arvada, CO (US); David Goodman, III, Federal Heights, CO (US)

(*) Notice: Subject to any disclaimer, the term of this patent is extended or adjusted under 35 U.S.C. 154(b) by 0 days.

(21) Appl. No.: 16/025,899

(22) Filed: Jul. 2, 2018

(51) Int. Cl.
*C07D 311/80* (2006.01)
*B01D 9/00* (2006.01)

(52) U.S. Cl.
CPC .......... *C07D 311/80* (2013.01); *B01D 9/005* (2013.01); *B01D 2009/0086* (2013.01); *C07B 2200/13* (2013.01)

(58) Field of Classification Search
CPC ... C07D 311/80; C07B 2200/03; B01D 9/005; B01D 2009/0086
USPC ........................................................ 549/390
See application file for complete search history.

(56) References Cited

U.S. PATENT DOCUMENTS

| | | |
|---|---|---|
| 6,630,507 B1 | 10/2003 | Hampson et al. |
| 6,840,999 B2 | 1/2005 | Liu et al. |
| 7,083,680 B2 | 8/2006 | Hamada |
| 7,700,368 B2 | 4/2010 | Flockhart et al. |
| 8,884,020 B2 | 11/2014 | Talley et al. |
| 9,186,386 B2 | 11/2015 | Speier |
| 9,512,118 B2 | 12/2016 | Yamamoto |
| 9,765,000 B2 | 9/2017 | Roura |
| 9,879,292 B2 | 1/2018 | Winnicki et al. |
| 2017/0008870 A1* | 1/2017 | Dibble ................ C07D 311/80 |

* cited by examiner

*Primary Examiner* — Taylor V Oh
(74) *Attorney, Agent, or Firm* — Carter, DeLuca & Farrell LLP

(57) ABSTRACT

A method for purifying crystals in a glass or metal container. A hydrocarbon is introduced into feed material containing tetrahydrocannabinol (THC). The feed material and hydrocarbon is placed in a glass or metal container. The hydrocarbon is then removed within a few minutes after introduction, leaving at least some hydrocarbon in the feed material. Pressure is allowed to build within the container in an oven or in a jacketed vessel for 2-3 weeks. During this time, THC acid crystals precipitate out and fall to the bottom of the container. The contents of the container are poured into a Buchner funnel and a vacuum is applied thereto in order to pull terpenes into a beaker. The terpenes are placed into an oven in order to purge off any remaining solvent. The funnel is then scraped to acquire THC acid crystals.

17 Claims, 1 Drawing Sheet

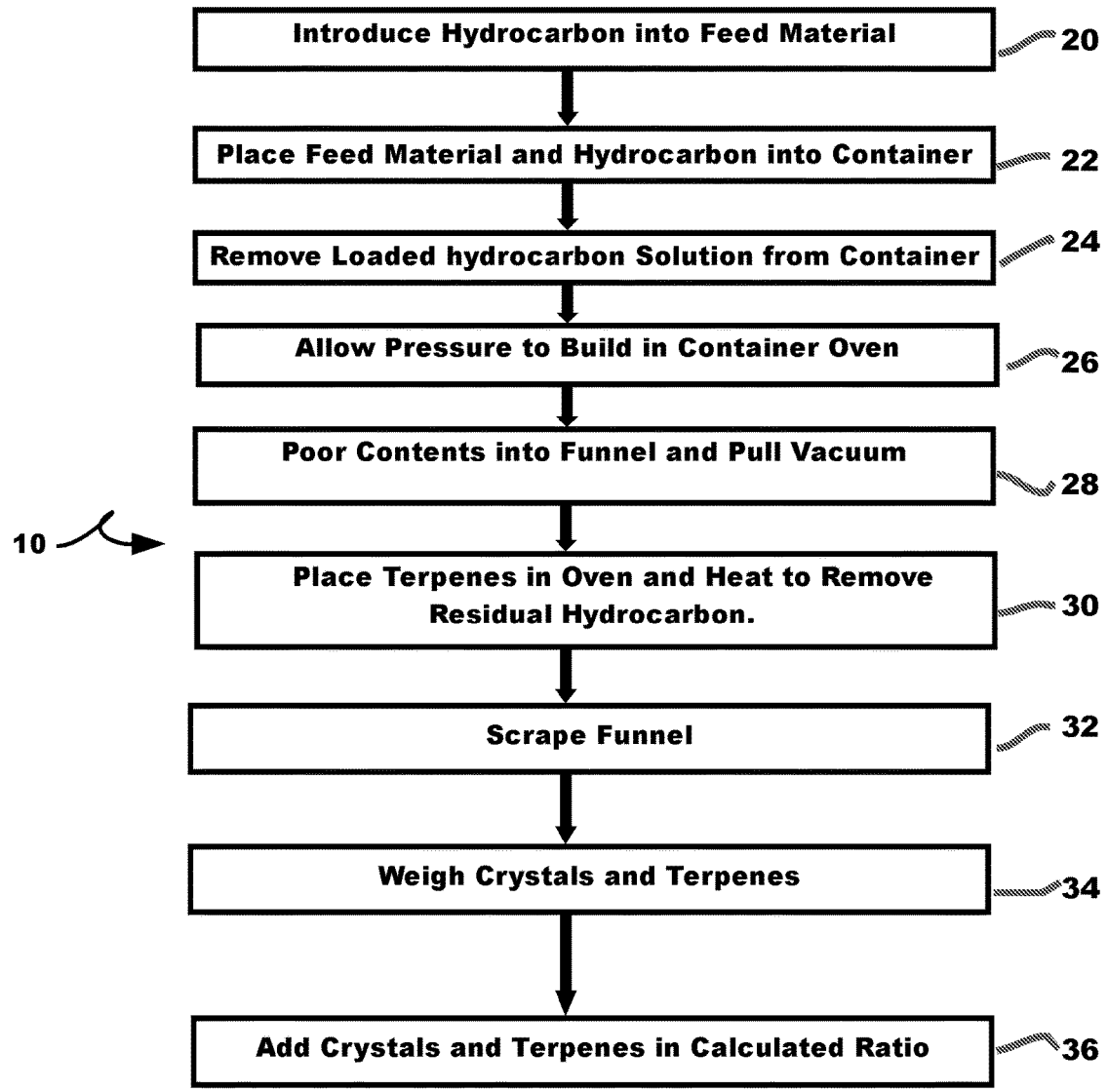

CRYSTAL PURIFICATION IN A GLASS OR METAL CONTAINER

RELATED PATENT APPLICATION

The present application is related to provisional patent application No. 62/543,792, for VAPOR-THIN FILM RECRYSTALLIZATION: A PROCESS FOR CRYSTAL PURIFICATION USING SOLVENT VAPORS THROUGH DYNAMIC EQUILIBRIUM RECRYSTALLIZATION filed Aug. 10, 2017, and hereby incorporates the teaching therein by reference.

FIELD OF THE INVENTION

This invention relates to a method for purifying crystals and, more particularly, to a method for purifying crystals in a glass or metal container through dynamic equilibrium recrystallization.

BACKGROUND OF THE INVENTION

*Cannabis*, more commonly known as marijuana, is a genus of flowering plants that includes at least three species: *cannabis sativa, cannabis* indica, and *cannabis ruderalis* as determined by plant phenotypes and secondary metabolite profiles.

The use of *cannabis* for social and medical purposes has been known for almost of all humanity's recorded history. *Cannabis* is most commonly administered via inhalation or consumption of marijuana-infused food and drink. However, since 1972 marijuana has been classified as a Schedule I drug under the U.S. Controlled Substances Act because the U.S. federal government considers it to have "no accepted medical use." In stark contrast to this position, a number of U.S. states and the District of Columbia have recognized the medical benefits of *cannabis* and have decriminalized its medical use.

In 2014, the U.S. Attorney General Eric Holder announced that the federal government would allow states to create a regime that would regulate and implement the legalization of *cannabis*, including loosening banking restrictions for *cannabis* dispensaries and growers.

The U.S. government has set a precedent for patenting *cannabis*, and *cannabis*-related inventions. For example, U.S. Pat. No. 6,630,507 issued on Oct. 7, 2003 and assigned on the patent face to The United States of America, is directed to methods of treating diseases caused by oxidative stress by administering therapeutically effective amounts of a cannabidiol (CBD) cannabinoid from *cannabis* that has substantially no binding to the N-methyl-D-aspartate (NMDA) receptor, wherein the CBD acts as an antioxidant and neuroprotectant. A search of the USPTO Patent Application Information Retrieval (PAIR) system reveals the existence of thousands of *cannabis* related applications and issued patents.

Despite the official position of the U.S. federal government, and as recognized by the states that have legalized it, *cannabis* has been shown to provide substantial benefits for medical and recreational uses. *Cannabis* is regularly used by a wide cross-section of society to treat a variety of maladies, conditions and symptoms including, but not limited to: nausea, glaucoma, lack of appetite, mucous membrane inflammation, epilepsy, leprosy, fever, obesity, asthma, urinary tract infections, coughing, anorexia associated with weight loss in AIDS patients, pain, and multiple sclerosis.

Cannabinoids are terpenophenolic compounds found in *cannabis sativa*, an annual plant belonging to the cannabaceae family. The plant contains more than 400 chemicals and approximately 70 cannabinoids. The latter accumulate mainly in the glandular trichomes. The most active of the naturally occurring cannabinoids is tetrahydrocannabinol (THC), which is used for treating a wide range of the aforementioned medical conditions.

Cannabidiol (CBD), an isomer of THC, is a potent antioxidant and anti-inflammatory compound known to provide protection against acute and chronic neuro-degeneration; cannabigerol (CBG), found in high concentrations in hemp, which acts as a high affinity; and cannabichromene (CBC), which possesses anti-inflammatory, anti-fungal and anti-viral properties. Many phytocannabinoids have therapeutic potential in a variety of diseases and may play a relevant role in plant defense as well as in pharmacology. Accordingly, biotechnological production of cannabinoids and cannabinoid-like compounds with therapeutic properties is of utmost importance. Thus, cannabinoids are considered to be promising agents for their beneficial effects in the treatment of various diseases.

One method of cannabinoid preservation includes separating a cannabinoid ethanol (EtOH) mixture from a *cannabis* extract through a filtration process, forming a slurry by combining a crystalline compound with the cannabinoid EtOH mixture, and heating and agitating the slurry in a pressurized chamber to form a colloidal cannabinoid EtOH mixture.

The colloidal cannabinoid EtOH mixture is distributed into a tray to form an evenly distributed mixture layer. An evaporation vessel is formed for the evenly distributed mixture layer through the attachment of a detachable cover to the tray, and the evaporation vessel is positioned and heated within a heating chamber. A rapid cooling process is performed as the evenly distributed mixture layer approaches saturation temperature, and this process is repeated until crystal formation is detected within the evenly distributed mixture layer. The evaporation vessel is removed from the heating chamber upon detection of crystal formation.

Recrystallizations of cannabinoids from solvents, in particular from non-polar hydrocarbon solvents, are well known in the art. These processes represent a classic recrystallization, where the solvent is heated to increase solubility of the compound to be recrystallized and then cooled, creating a supersaturated solution that grows crystals.

Other recrystallization processes include using a second, weak solvent that, when added to the saturated solvent, causes precipitation of crystals. Still other, less common recrystallization techniques exist for specialized crystal growth, such as those made for protein crystallography where a reactant is added to the solvent, producing a compound as it crystallizes.

In all cases, crystal growth is limited by the ability of the molecule to move into regularly ordered, crystalline structures while excluding impurities, without re-dissolving the growing crystals. If heat is applied, the solubility of the compound increases in the solvent and crystallization is limited. Kinetic energy as vibration can be applied, short of heating the solution, to provide kinetic energy for mass transfer without heat. Electrical potentials have been applied to crystal growth, enhancing the process under controlled conditions.

These processes rely on successive recrystallization passes that break down or destroy the previous crystal, release included impurities, and grow a new crystal that is more pure due to dilution of impurities in the solvent during the destruction phase. Crystal manufacturing processes prefer growing by deposition of new material, not purification by rearrangement because their process involves growth, destruction and regrowth. Time for growth has been the limiting factor in performing the recrystallization methods.

Conventionally, crystals and terpenes are not separated, as manufacturers typically are not concerned about having solvent left over after a purification process. Grams of crystals are produced from a mason jar, each gram appearing and being different from one another. The inventors have found, however, that separating, weighing, and then recombining the crystals and terpenes results in each crystal being substantially identical to each other.

DESCRIPTION OF RELATED ART

U.S. Pat. No. 6,840,999 issued to Liu, et al. on Jan. 11, 2005 for IN SITU REGROWTH AND PURIFICATION OF CRYSTALLINE THIN FILMS discloses a method of recrystallizing amorphous or polycrystalline films into single-crystal thin films (of micrometer thickness) by a zone melting technique, in which an electrically heated wire generated a narrow heated or molten zone (0.5-2 mm wide) on the substrate sandwiched between two pieces of glass or indium-tin-oxide-coated glass. The substrate can be either an organic or inorganic compound. When the molten zone is moved slowly (3-120 µm/min) across the layer from one end of the cell to the other, a single-crystal film is produced after a single pass. This technique allows for thin film purification and an improvement in electronic, optical, and optoelectronic properties of the thin film.

U.S. Pat. No. 7,083,680 issued to Hamada on Aug. 1, 2006 for SUBLIMATION AND PURIFICATION METHOD discloses a method of locating a glass bottle containing a sample of an organic material to be purified at a position surrounded by a heater near one end in an outer glass tube. An inner glass tube for catching organic crystals obtained by recrystallization is located at a position near the other end in the outer glass tube. When the sample of the organic material is sublimed and purified, the inside of the outer glass tube is kept in a higher vacuum state (lower pressure) than 200 Pa by a vacuum pump. The sample inside the outer glass tube is heated by the heater, to sublime organic molecules of the sample contained in the glass bottle. The outer glass tube is provided with a temperature gradient, so that organic molecule vapor is cooled near the other end in the outer glass tube, and is recrystallized inside the inner glass tube.

U.S. Pat. No. 7,700,368 issued to Flockhart, et al., on Apr. 20, 2010 for METHODS OF PURIFYING CANNABINOIDS FROM PLANT MATERIAL discloses methods of preparing cannabinoids in substantially pure form starting from plant material. Also described are substantially pure preparations of various cannabinoids and cannabinoid acids, and also extracts enriched in cannabinoids and cannabinoid acids.

U.S. Pat. No. 8,884,020 issued to Talley, et al., on Nov. 11, 2014 for INDOLE COMPOUNDS discloses indole derivatives that are useful for treating pain, inflammation and other conditions. Certain of the compounds are benzyl derivatives and others are benzoyl derivatives. The compounds are substituted at least at the 3 position of the indole.

U.S. Pat. No. 9,186,386 issued to Speier, on Nov. 17, 2015 for PHARMACEUTICAL COMPOSITION AND METHOD OF MANUFACTURING discloses methods of obtaining an extract of *cannabis* plant material as well as subsequent processing of the extract to provide a concentrate of *cannabis*. Also described are pharmaceutical dosage forms (e.g., oral thin films and transdermal patches) that include the concentrate (or extract) of *cannabis*, as well as methods of medical treatment that include administering the pharmaceutical dosage forms.

U.S. Pat. No. 9,512,118 issued to Yamamoto, on Dec. 6, 2016 for CRYSTAL OF FUSED HETEROCYCLIC COMPOUND discloses a crystal of 1-ethyl-7-methyl-3-{4-[(3-methyl-3H-imidazo[4,5-b]pyridin-2-yl)oxy]phenyl-}-1,3-dihydro-2H-imidazo[4,5-b]pyridin-2-one useful as a prophylactic or therapeutic agent for schizophrenia and the like, which shows an X-ray powder diffraction pattern having characteristic peaks at interplaner spacings (d) of 13.59 plus or minus 0.2 and 6.76 plus or minus 0.2 Angstroms in powder X-ray diffraction.

U.S. Pat. No. 9,765,000 issued to Nadal Roura, on Sep. 19, 2017 for METHODS OF PURIFYING CANNABINOIDS, COMPOSITIONS AND KITS THEREOF discloses methods of purifying one or more cannabinoids from a plant material, purified cannabinoids and pharmaceutical compositions comprising one or more cannabinoids produced by the disclosed method, methods and uses for treating a disease or condition employing such purified cannabinoids and pharmaceutical compositions.

U.S. Pat. No. 9,879,292 issued to Winnicki, et al., on Jan. 30, 2018 for APPARATUS AND METHODS FOR BIOSYNTHETIC PRODUCTION OF CANNABINOIDS discloses an apparatus and methods for producing tetrahydrocannabinolic acid (THCA), cannabichromenic acid (CBCA) and cannabichromenic acid (CBCA) in different ratios. The apparatus comprises: (i) a bioreactor comprising (a) an automated supply system configuredto deliver a first automated supply of cannabigerolic acid (CBGA), a cannabinoid acid synthase, and a reaction mixture; and (b) a second automated system to cease the reaction; (ii) a controller configured to modify a property of the reaction mixture to produce the desired products; and (iii) an extractor configured to recover the tetrahydrocannabinolic acid (THCA), cannabichromenic acid (CBCA) or cannabidiolic acid (CBDA) and cannabichromenic acid.

SUMMARY OF THE INVENTION

While recrystallization from a super-saturated solution is well understood, the present invention allows crystal rearrangement and purification to take place in the vapor and/or liquid film covering the crystals. Mass transfer takes place at the interface of the vapor/liquid film on the crystals, allowing the molecules to rearrange and purify. In the present invention, crystals purify by rearrangement, not by growth in mass, allowing for a single recrystallization pass as opposed to convention, sequential recrystallizations, each taking three to seven days. Moreover, traditional recrystallization suffers from losses of the starting crystal to the solvent that is not recrystallized at each step, which can be recovered later but represent an "apparent loss" during a single recrystallization cycle that accumulates during multiple recrystallization steps.

Compounds dissolve into solution, but solvents can also dissolve onto crystals, much like desiccants attract and hold water. Strong desiccants can hydrate to point of a thin film of water covers the mass. This is also true of other solvent vapors that are strongly attracted to solids, such as butane attracted to cannabinoids, essential oils, and other plant components. The extract mass becomes "wet" in the atmosphere of saturated hydrocarbon vapors, and the impurities (essential oils, neutral cannabinoids, etc.) are more strongly attracted to a hydrocarbon solvent than the acid forms of the cannabinoids. This allows the impurities to attract more solvent, become wetter, and flow down the sides of the vessel while allowing the cannabinoid acid form molecules to be incorporated into the rearranging crystals as they increase in purity. Neutral forms of cannabinoids are more soluble and are drained away from the crystal with the other more soluble impurities.

This is not the same as washing the crystals with butane liquid formed within a vessel by reflux (i.e., evaporating the solvent in a hot zone and re-condensing the solvent in a cool zone above the crystals to allow the fresh solvent to wash the surface of the crystals). The solvent reflux method of the present invention removes impurities from the surface of crystals from the previous recrystallization, but does not facilitate mass transfer and purification through dynamic equilibrium recrystallization. Reflux is a process driven by evaporation and condensation.

The reflux process can provide enough solvent to dissolve the crystals entirely and wash them down the surface of the vessel. Such a method does not allow for the time for crystal growth afforded by a resident thin-layer of vapor deposited solvent. The degree of solvent film on the surface of the crystal, and the slope of vessel wall for impurity draining from the crystalline mass must be controlled to allow the crystals time to purify through recrystallization, but not re-dissolve them in solvent or wet the crystals enough to wash them down the vessel.

As seen with live resin extraction runs, the high levels of terpenes in the extract pull additional hydrocarbon solvent into the crystalline mass so strongly that the increase in solvent in the mass rinses it down the wall of the vessel. As the impurities increase in the flow of solvent down the mass, the solution pulls in additional solvent, making it thinner and improving the flow. Butane liquid flowing down is replaced by solvent vapors in equilibrium on the surface of the fresh crystal. This process is driven by solubility, not evaporation and condensation.

Once the surface film of solvent is deposited onto the crystal molecules from the crystal dissolve, and the layer of solvent becomes saturated. The layer is not flushed away as in a reflux rinsing method, but stationary so that dynamic equilibrium results, where molecules and impurities can leave the crystal into the solvent, and molecules can come back onto the crystal, allowing for crystal purification without increases in mass as in other recrystallization methods. If an excess of solvent is used, the crystal dissolves into the solvent and is rinsed away without residence time for dynamic equilibrium recrystallization purification.

In accordance with the present invention, there is provided a method for purifying crystals in a glass or metal container. A hydrocarbon is introduced into feed material containing tetrahydrocannabinol (THC). The feed material and hydrocarbon is placed in a glass or metal container. The hydrocarbon is then removed within a few minutes after introduction, leaving at least some hydrocarbon in the feed material. Pressure is allowed to build within the container in an oven or in a jacketed vessel for 2-3 weeks. During this time, THC acid crystals precipitate out and fall to the bottom of the container. The contents of the container are poured into a Buchner funnel and a vacuum is applied thereto in order to pull terpenes into a beaker. The terpenes are placed into an oven in order to purge off any remaining solvent. The funnel is then scraped to acquire THC acid crystals.

It is therefore an object of the invention to provide a method for purifying crystals.

It is a further object of the present invention to provide a method for purifying crystals that uses solvent vapor in a recrystallization process.

It is a further object of the present invention to provide a method for purifying crystals, leaving purified crystals in a glass or metal container.

These and other objects and advantages of the present invention are more readily apparent with reference to the following detailed description and the accompanying drawings.

BRIEF DESCRIPTION OF THE DRAWINGS

A complete understanding of the present invention may be obtained by reference to the accompanying drawings, when considered in conjunction with the subsequent detailed description, in which:

FIG. 1 is a flow chart of system operations.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

The invention includes the following steps. Hydrocarbon is introduced into feed material containing tetrahydrocannabinol (THC). The feed material and hydrocarbon is placed in a glass or metal container. The hydrocarbon is then removed within a few minutes after introduction, leaving at least some hydrocarbon in the feed material. Pressure is allowed to build within the container in an oven or in a jacketed vessel for 2-3 weeks. During this time, THC acid crystals precipitate out and fall to the bottom of the container. The contents of the container are poured into a Buchner funnel and a vacuum is applied thereto in order to pull terpenes into a beaker. The terpenes are placed into an oven in order to purge off any remaining solvent. The funnel is then scraped to acquire THC acid crystals.

Although a glass container can be used in the practice of the current invention, a metal container, specifically a stainless steel vessel, has been found to be most effective. A basic steel vessel should preferably have a sight glass for observing the process and formation of the purified crystals, a pressure meter, a clamped lid, and means for adjusting the pressure and solvent.

Referring now to FIG. 1, a flow chart of operations is shown generally at reference numeral 10.

A hydrocarbon is introduced into feed material containing tetrahydrocannabinol (THC), step 20. The feed material and hydrocarbon is placed in a glass or metal container, step 22. The loaded hydrocarbon solution is then removed from the container within a few minutes after introduction, leaving at least some hydrocarbon in the feed material, step 24.

Pressure is allowed to build within the container in an oven or in a jacketed vessel for 2-3 weeks, step 26. During this time, THC acid crystals precipitate out and fall to the bottom of the container. The contents of the container are poured into a Buchner funnel and a vacuum is applied thereto, step 28, in order to pull terpenes into a beaker.

The terpenes are placed into an oven, step 30, in order to purge off any remaining residual hydrocarbon. The funnel is scraped to acquire THC acid crystals, step 32.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A method for purifying tetrahydrocannabinol (THCa) crystals in a glass or metal container, the steps comprising:
 a) introducing a hydrocarbon into feed material containing THCa;
 b) placing the feed material and hydrocarbon in a glass or metal container, forming a loaded hydrocarbon solution;
 c) removing the loaded hydrocarbon solution, leaving at least some hydrocarbon in the feed material in the container;
 d) allowing pressure to build within the container in an oven or in a jacketed vessel;
 e) pouring the contents of the container into a funnel;
 f) drawing a vacuum in the container in order to extract terpenes therefrom;
 g) placing the terpenes into an oven to apply heat thereto in order to purge off residual hydrocarbon; and
 h) scraping the funnel to acquire THCa acid crystals.

2. The method for purifying THCa crystals in a glass or metal container in accordance with claim 1, wherein the feed material comprises fresh frozen feed material.

3. The method for purifying THCa crystals in a glass or metal container in accordance with claim 1, wherein the funnel comprises a Buchner funnel.

4. The method for purifying THCa crystals in a glass or metal container in accordance with claim 1, wherein the hydrocarbon comprises butane.

5. The method for purifying THCa crystals in a glass or metal container in accordance with claim 1, the steps further comprising:
 i) weighing the THCa crystals and the terpenes; and
 j) determining a ratio of THCa crystals to terpenes required for each container/gram.

6. The method for purifying THCa crystals in a glass or metal container in accordance with claim 5, the steps further comprising:
 k) adding sufficient THCa crystals and terpenes in the ratio thereof to obtain a full gram of THCa crystals so that every gram thereof has an identical percentage of purity.

7. A method for purifying tetrahydrocannabinol (THCa) crystals in a glass or metal container, the steps comprising:
 a) placing a hydrocarbon into feed material containing THCa in a glass or metal container, forming a loaded hydrocarbon solution;
 b) removing the loaded hydrocarbon solution, leaving at least some hydrocarbon in the feed material in the container;
 c) applying heat to the contents of the container in an oven or in a jacketed vessel;
 d) pouring the contents of the container into a funnel;
 e) drawing a vacuum in the container in order to extract terpenes therefrom;
 f) placing the terpenes into an oven to apply heat thereto in order to purge off residual hydrocarbon.

8. The method for purifying THCa crystals in a glass or metal container in accordance with claim 7, wherein the feed material comprises fresh frozen feed material.

9. The method for purifying THCa crystals in a glass or metal container in accordance with claim 7, wherein the funnel comprises a Buchner funnel.

10. The method for purifying THCa crystals in a glass or metal container in accordance with claim 7, wherein the hydrocarbon comprises butane.

11. The method for purifying THCa crystals in a glass or metal container in accordance with claim 7, the steps further comprising:
 g) weighing the THCa crystals and the terpenes; and
 h) determining a ratio of THCa crystals to terpenes required for each container/gram.

12. The method for purifying THCa crystals in a glass or metal container in accordance with claim 11, the steps further comprising:
 i) adding sufficient crystals and terpenes in the ratio thereof to obtain a full gram of THCa crystals so that every gram thereof has an identical percentage of purity.

13. The method for purifying THCa crystals in a glass or metal container in accordance with claim 1, wherein allowing pressure to build within the container in an oven or in a jacketed vessel includes allowing pressure to build within the container in an oven or in a jacketed vessel for between two to three weeks.

14. The method for purifying THCa crystals in a glass or metal container in accordance with claim 13, wherein allowing pressure to build within the container in an oven or in a jacketed vessel for between two to three weeks occurs prior to pouring the contents of the container into the funnel.

15. The method for purifying THCa crystals in a glass or metal container in accordance with claim 7, further comprising allowing pressure to build within the container in an oven or in a jacketed vessel.

16. The method for purifying THCa crystals in a glass or metal container in accordance with claim 15, wherein allowing pressure to build within the container in an oven or in a jacketed vessel includes allowing pressure to build within the container in an oven or in a jacketed vessel for between two to three weeks.

17. The method for purifying THCa crystals in a glass or metal container in accordance with claim 16, wherein allowing pressure to build within the container in an oven or in a jacketed vessel for between two to three weeks occurs prior to pouring the contents of the container into the funnel.

* * * * *